(12) United States Patent
Kettler

(10) Patent No.: US 7,248,350 B2
(45) Date of Patent: Jul. 24, 2007

(54) NON-DESTRUCTIVE METHOD OF DETERMINING THE REFRACTIVE INDEX OF CLEAR COATS

(75) Inventor: Wilhelm Kettler, Wuppertal (DE)

(73) Assignee: E. I. du Pont de Nemours and Company, Wilmington, DE (US)

(*) Notice: Subject to any disclaimer, the term of this patent is extended or adjusted under 35 U.S.C. 154(b) by 458 days.

(21) Appl. No.: 10/832,856

(22) Filed: Apr. 27, 2004

(65) Prior Publication Data

US 2005/0237515 A1    Oct. 27, 2005

(51) Int. Cl.
*G01N 21/41* (2006.01)

(52) U.S. Cl. .................................. 356/128
(58) Field of Classification Search ............. 356/128, 356/319
See application file for complete search history.

(56) References Cited

U.S. PATENT DOCUMENTS

| | | | |
|---|---|---|---|
| 3,916,168 A | 10/1975 | McCarty et al. | |
| 4,479,716 A | 10/1984 | Alman | |
| 5,042,949 A * | 8/1991 | Greenberg et al. | 356/451 |
| 5,414,506 A * | 5/1995 | Saisho et al. | 356/128 |
| 5,754,283 A | 5/1998 | Keane et al. | |
| 5,956,133 A * | 9/1999 | Imura | 356/446 |
| 6,064,487 A | 5/2000 | Kettler et al. | |
| 6,288,172 B1 | 9/2001 | Goetz et al. | |
| 6,583,879 B1 * | 6/2003 | Berg et al. | 356/402 |
| 6,801,321 B1 * | 10/2004 | Du-Nour | 356/504 |
| 2004/0252883 A1 | 12/2004 | Johansson et al. | |

FOREIGN PATENT DOCUMENTS

| | | |
|---|---|---|
| DE | 4243885 A1 | 6/1994 |
| EP | 0932038 A1 | 7/1999 |
| JP | 2004-361382 | * 12/2004 |

OTHER PUBLICATIONS

European Search Report, Application No. EP 05008719, mailed Jul. 1, 2005.

* cited by examiner

*Primary Examiner*—Gregory J. Toatley, Jr.
*Assistant Examiner*—Kara Geisel
(74) *Attorney, Agent, or Firm*—Sudhir G. Deshmukh

(57) ABSTRACT

The invention is directed to a method for determining repairability of an original clear coat applied over a darkly pigmented substrate with a corresponding repair clear coat used in repairing damaged original vehicle coatings. The method non-destructively determines the refractive indices of the original clear coat and the corresponding repair clear coats by acquiring the reflection spectrum of these coats with a spectrophotometer with d/8° measurement geometry with and without the specular components followed by determining the refractive indices with the assistance of the differential spectrum between the reflection spectrums with and without the specular components, and then comparing the refractive indices to determine difference between these refractive indices, wherein when the difference between the refractive indices of the original arid repair clear coats is within an acceptable range, the repair clear coat is used for repairing the original clear coat.

5 Claims, 5 Drawing Sheets

NON-DESTRUCTIVE METHOD OF DETERMINING THE REFRACTIVE INDEX OF CLEAR COATS

FIELD OF THE INVENTION

The invention relates to a method for the non-destructive determination of the refractive index of clear coats and binder systems. The method may in particular be used to facilitate determination of the repairability of clear coats applied in vehicle original coating using corresponding repair clear coats.

DESCRIPTION OF RELATED ART

The appearance of any object colour is determined by the optical properties of its surface and the pigmentation of the paint layer. The former reflection phenomenon is governed by the refractive index n of the medium and the topography or texture of the boundary layer, respectively. In the course of vehicle repair coating, damaged original vehicle coatings are touched up with corresponding repair coatings. It is necessary for the repair coating to match the colour shade of the original coating as exactly as possible. Especially where repair coatings are applied within a surface, i.e., within a vehicle component where there is a direct transition between the original and repair coating and these coatings are not separated from one another by any structural boundaries, accurate colour matching is particularly important since even relatively small differences are noticeable by an observer.

In addition to accurate colour matching (pigmenting), however, reflective properties (gloss, refractive index) of the coating surface are also very important for overall optical appearance. Colour differences are apparent and blushing is perceived especially for dark shades if the difference in gloss or in refractive index between the original coating and repair coating exceeds a specific threshold value.

This means that while inadequate colour matching of a base coating may be improved by further tinting steps, the refractive index of a clear coat is a property of the coating used and cannot be improved or modified by external measures. This in turn means that when an appropriate repair clear coat is being selected, it is necessary to take into account of whether this clear coat is suitable with regard to its refractive index for repairing the original clear coat.

The difference Δn in refractive index between two clear coats ought to be less than 0.04 to guarantee that even for black or very dark colour shades the different surface reflection properties of both materials are not perceptible by any observer. So the refractive index can be used for adjustment between OEM and Refinish paint material. In particular, in polyester clear coats having a low refractive index there was always a need for justification of the fact that gloss levels above 90 can not be achieved.

If it is to be possible to assess the repairability of original coatings with corresponding repair coatings with the assistance of the refractive index, the refractive indices of the original and repair coatings must be known.

The refractive index n is not directly measurable, but must be derived from measurable quantities (e.g., reflection and transmission coefficients, reflectances and transmittances, and angle of refraction) by imposing a suitable theory. At a given wavelength there are, in general, two optical constants n and k to be determined, that both can be combined into a single complex number $$N = n + ik$$

termed as the complex refractive index of a material. The imaginary part, k, is frequently referred to as the extinction coefficient, and n is called the refractive index. This implies that two or more measurements are required to experimentally determine both (coupled) optical constants. Several experimental methods for the determination of optical constants such as refractive index of non-absorbing materials have been developed. The following methods may be used for this purpose:

1. Measurement of refraction angles, such as the angle of minimum deviation of a prism; n is obtained from Snell's law. This method requires samples of high transparency ($k \approx 0$).
2. Measurement of the transmittance and reflectance of a slab for light at near-normal incidence. The samples must be sufficiently transparent for measurable transmission in thin slabs, but not as transparent as required in method 1.
3. Measurement of reflectance at near-normal incidence over a wide range of frequencies. The phase shift of the reflected light is obtained from a Kramers-Kronig analysis. This technique is of great value in spectral regions where the sample is highly opaque, but requires measurements over an extended region and extrapolations into unmeasured regions.
4. Ellipsometric techniques in which amplitude ratios and phase shifts for reflected light are directly measured as opposed to the previous technique in which the phase shift is directly obtained. This is difficult to do over large wavelength regions because of requirements on optical elements, such as polarisers and retarders.
5. Measurement of reflectances for incident light of various polarisation states and two oblique angles of incidence. The results are analysed with the Fresnel formulae. Large angles are required for high accuracy, and this in turn requires large sample surfaces.

Apart from method 4, measurement is generally performed in the stated methods on self-contained free films, which is relatively complex because the self-contained free films must first be produced by application and subsequent removal.

If self-contained thin films of the material are available, their refractive index can be measured easily by means of a refractometer. Generally, such measuring systems provide refractive indices integrated over the visible spectral range. But the preparation of self-contained clear coats requires some intuition to arrive at reliable results. While method 4 does not require any self-contained free films, it is very costly and also very time-consuming.

There is accordingly a requirement for a relatively straight-forward non-destructive method for determining the refractive index of clear coats and binder systems to determine in advance the repairability of original coatings with corresponding repair coatings.

SUMMARY OF THE INVENTION

The present invention accordingly relates to a method for the non-destructive determination of the refractive index of un-pigmented or transparently pigmented coatings or of binder systems comprising the following steps:

A) application of a transparent layer of an un-pigmented or transparently pigmented coating or an un-pigmented binder system onto a darkly pigmented substrate;

B) optional drying and/or curing of the coating obtained;

C) acquisition of the reflection spectrum of the coating obtained with a spectrophotometer with d/8° measurement geometry with the specular component included and with the specular component excluded;

D) determination of the differential spectrum between the reflection spectrum with the specular component included and the reflection spectrum with the specular component excluded; and E) determination of the refractive index of the coating or binder system with the assistance of the differential spectrum obtained in D) by making use of a previously determined relationship between the difference in the reflection spectrum with the specular component included and the reflection spectrum with the specular component excluded of the coating or binder system and the refractive index of the corresponding coating or binder system.

The transparent layer of an un-pigmented or transparently pigmented coating or binder system is preferably applied onto a black pigmented substrate.

DETAILED DESCRIPTION OF THE EMBODIMENTS

The refractive index of clear coats is of fundamental importance for the development of deep black surface coatings and for indicating the repairability of dark colour shades, respectively. This optical material parameter determines the fraction of light incident on a surface coating that in any case is reflected back into the surrounding medium, usually air.

The present invention provides a non-destructive method by spectrophotometry that requires only a panel covered with a carbon black pigmented layer and the clear coat or the binder system to be characterised. The spectrophotometer has to be equipped with an integrating (Ulbricht) sphere of the measuring geometry d/8° that allows for reflectance measurements with the specular component included ($R_{SPIN}(\lambda)$) and with the specular component excluded ($R_{SPEX}(\lambda)$), respectively. The difference spectrum $$\Delta R(\lambda) = R_{SPIN}(\lambda) - R_{SPEX}(\lambda)$$

of both measuring quantities depends only on the refractive index n of the clear coat.

In step A of the method according to the invention, a transparent layer of an un-pigmented or transparently pigmented coating or an un-pigmented binder system is applied onto a darkly pigmented, preferably black pigmented substrate. Application proceeds in conventional manner, for example, by means of spray application. The composition of the un-pigmented or transparently pigmented coating here respectively corresponds, for example, with regard to binder, crosslinking agent, organic solvents, water and/or conventional coating additives, to that of the original clear coat to be repaired and to that of the repair clear coat intended for the repair. Alternatively, if necessary, an un-pigmented binder system may also be used instead of the clear coat.

In step B of the method according to the invention, the applied coating layer or binder layer is preferably dried or cured. In principle, however, the following measurements in the method according to the invention may also be performed on the undried/uncured wet coating layer.

In step C of the method according to the invention, the reflection spectrum with the specular component included and the reflection spectrum with the specular component excluded are acquired from the coating obtained by means of a spectrophotometer. As already mentioned above, the spectrophotometer must be equipped with an integrating sphere with d/8° measurement geometry.

Figure 1:
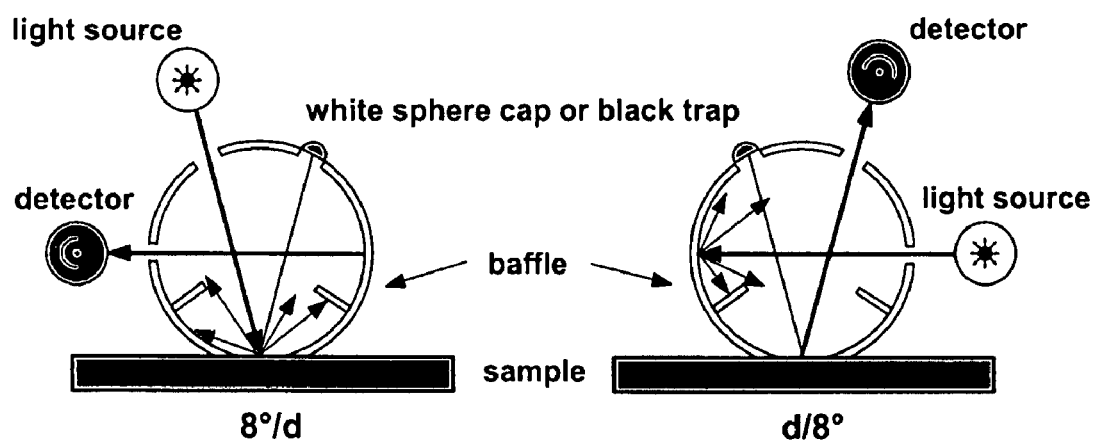
FIG. 1 shows a typical integrating sphere used in reflectance spectroscopy.

A typical integrating sphere used in reflectance spectroscopy for attaining hemispherical illumination or hemispherical collection is a hollow spherical construction containing several small excitation and emission ports (see FIG. 1). In FIG. 1 standard d/8° and 8°/d measurement geometries, respectively, are shown recommended by technical standards (as, e.g., DIN 5033) to be used for glossy and matt solid colour shades.

The sphere is coated inside with a spectrally non-selective (white) material (e.g., barium sulphate paint) of high diffuse reflectance. The radiant power from the radiation source incident through one of the ports is geometrically distributed in a uniform manner due to multiple reflections at the sphere wall. If the fraction of radiation directionally reflected from the sample surface at an angle of 8° with respect to the surface normal is absorbed or allowed to escape from the sphere by using a gloss trap, solely the radiation diffusely reflected from the sample interior will contribute to the measurement signal (specular excluded measurement mode (SPEX)). Replacing the gloss trap by a spherical cap covered with the same matte-white coating than the rest of the sphere will include this specularly reflected surface component into the measurement signal (specular included measurement mode (SPIN)).

A small baffle in the integrating sphere placed between the specimen and the spot of the sphere wall illuminated or viewed, reduces the possibility of superimposing on the specimen or the spot on the sphere wall a component of directly reflected flux. The directly reflected flux would to some extent upset the desired diffuse illumination or viewing condition. In case of a sample exhibiting an arbitrary surface texture, for the difference spectrum the inequality $\Delta R(\lambda) = R_{SPIN}(\lambda) - R_{SPEX}(\lambda) \geq 0$ holds. The lower limit is approached when measuring a sample of almost ideal matt surface structure. The other extreme case corresponds to samples having a smooth surface and will lead to a finite difference signal, depending solely on the refractive index n of the embedding medium.

The described experimental illuminating and viewing arrangement is one of the standard conditions for colour measurement recommended by the CIE (CIE=Commision internationale de l'éclairage). Appropriate equipment is therefore standard instrumentation for a coloristic laboratory.

Then, in step D) of the method according to the invention, the differential spectrum between the reflection spectrum with the specular component included and the reflection spectrum with the specular component excluded is determined.

Finally, in step E) of the method according to the invention, the refractive index of the coating or binder system is determined with the assistance of the differential spectrum obtained in D) by making use of the previously determined relationship between the difference between the reflection spectrum with the specular component included and the reflection spectrum with the specular component excluded of the coating or binder system and the refractive index of the corresponding coating or binder system.

Figure 2:
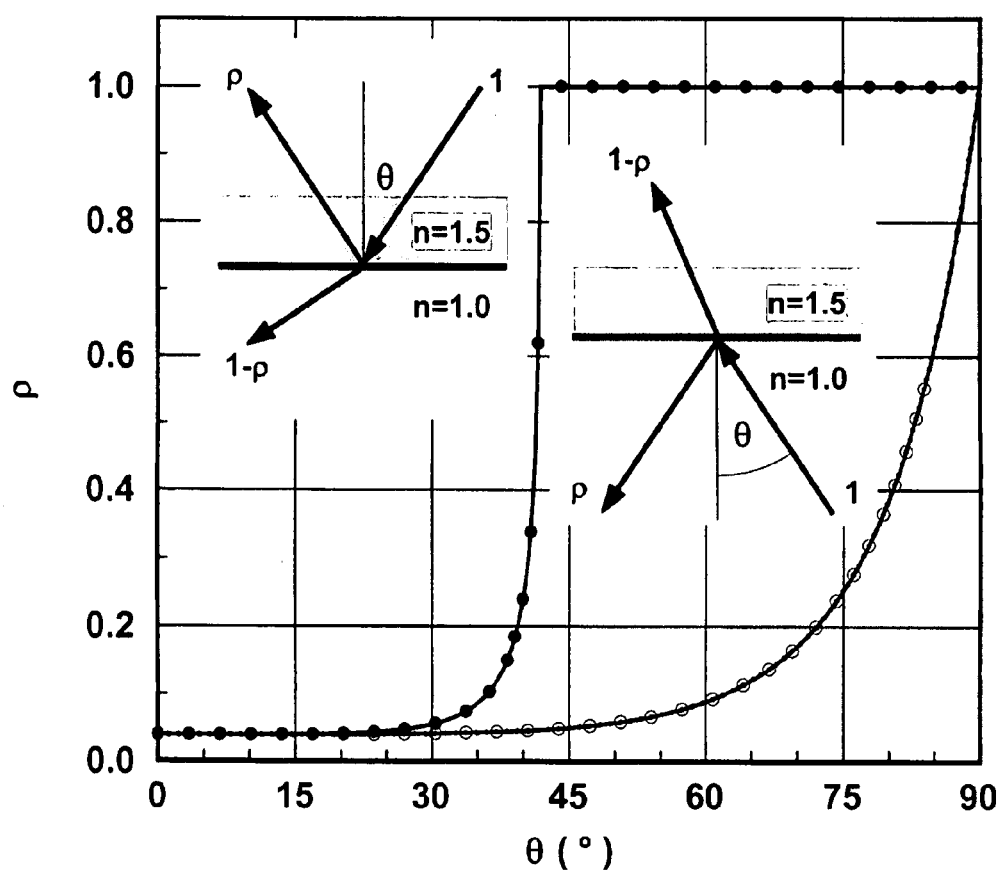
FIG. 2 shows Fresnel reflection of a non-absorbing material for totally depolarised incident light on both sides of a boundary layer.

The formulaic relationship between the difference between the reflection spectrum with the specular component included and the reflection spectrum with the specular component excluded and the refractive index of a coating or binder system is as follows:

The reflectivity ρ at the boundary interface may be calculated from Fresnel's equations. For radiation externally incident on the surface at an angle θ with the normal, the reflectivity averaged over the two components of polarisation is given by $$\rho = \frac{1}{2}\left[\left(\frac{\sqrt{n^2 - \sin^2\theta} - \cos\theta}{\sqrt{n^2 - \sin^2\theta} + \cos\theta}\right)^2 + \left(\frac{n^2\cos\theta - \sqrt{n^2 - \sin^2\theta}}{n^2\cos\theta + \sqrt{n^2 - \sin^2\theta}}\right)^2\right]$$

where n is the ratio of the refractive indices of the matrix and the surroundings. When a beam is incident on the interface from the matrix side, ρ may be calculated from the above equation by substituting 1/n for n, for all θ less than $\sin^{-1}(1/n)$; above this angle, the beams undergo total internal reflection and ρ=1. The angular variation of ρ for both cases is depicted in FIG. 2. FIG. 2 shows Fresnel reflection of a non-absorbing material for totally depolarised incident light on both sides of the boundary layer. A beam incident at an angle corresponding to $\mu_o = \cos\theta_o$ will be partially reflected. The direction $\mu_o'$ of the component entering the matrix may be calculated from Snell's law $$\sqrt{1 - \mu_o'^2} = \frac{1}{n}\sqrt{1 - \mu_o^2}.$$

In the limit of perpendicularly incident radiation (θ=0) the above expression for ρ simplifies considerably to $$\rho = \left(\frac{n-1}{n+1}\right)^2.$$

Since the Fresnel equations exhibit only a weak angle-dependence in the close proximity of the surface normal, the difference spectrum ΔR(λ) can be approximated and expressed analytically by Fresnel's equation for normal incidence of light $$\Delta R(\lambda) \approx \left(\frac{n(\lambda) - 1}{n(\lambda) + 1}\right)^2$$

that can easily be transformed to give the refractive index $$n(\lambda) = \frac{1 + \sqrt{\Delta R(\lambda)}}{1 - \sqrt{\Delta R(\lambda)}}$$

itself. This method allows directly for a wavelength-dependent determination of n. The error Δn of the calculated refractive index, n, can be estimated from the error of the measured reflectance values according to $$\Delta n_\lambda = \pm \left|\frac{\partial n_\lambda}{\partial(\Delta R_\lambda)}\delta(\Delta R_\lambda)\right|$$

with the enhancement factor $$\frac{\partial n_\lambda}{\partial(\Delta R_\lambda)} = \frac{1}{\sqrt{\Delta R_\lambda}\left(1 - \sqrt{\Delta R_\lambda}\right)^2}.$$

Figure 3:
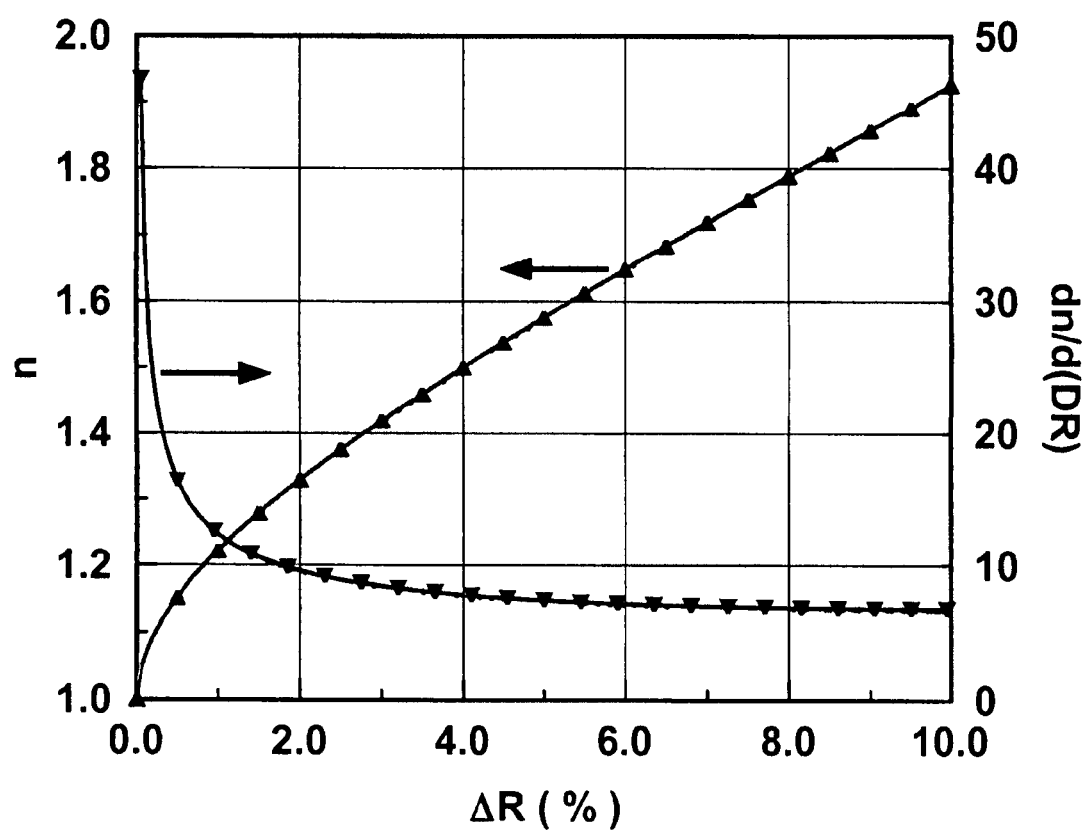
FIG. 3 shows the refractive index n as a function of a difference spectrum $\Delta R = R_{SPIN} - R_{SPEX}$.

FIG. 3 shows the refractive index n as a function of difference spectrum $\Delta R = R_{SPIN} - R_{SPEX}$.

As can be seen from FIG. 3 within the usual range of refractive indices of clear coats the error of the reflectance is enhanced by roughly a factor of 8. A typical reflectance error of 0.3% will result in an error of 2.4% for the refractive index, i.e., $\Delta n_\lambda \approx \pm 0.04$. However, the relative error of the data is much smaller.

The total reflectance for the specular included measurement condition, $R_{SPIN}$, according to $$R_{SPIN} = r_{d,\Omega-\Delta\Omega} + r_{d,\Delta\Omega} + r_{s,\Delta\Omega}$$

can be divided into three different contributions. The sum of the first two diffuse reflectance terms equals the total diffuse reflectance, where $r_{d,\Delta\Omega}$ denotes the fraction reflected into the solid angle ΔΩ of the black trap, and $r_{d,\Omega-\Delta\Omega}$ the fraction reflected into the remaining solid angle Ω−ΔΩ. The surface reflection contribution is given by $r_{s,\Delta\Omega}$. Exclusion of the specular component from the measurement signal leads to the equation $$R_{SPEX} = r_{d,\Omega-\Delta\Omega}$$

so that the combined difference spectrum $$\Delta R = R_{SPIN} - R_{SPEX} = r_{s,\Delta\Omega}\left(1 + \frac{r_{d,\Delta\Omega}}{r_{s,\Delta\Omega}}\right)$$

can be approximated by $r_{s,\Delta\Omega}$ if the condition $r_{d,\Delta\Omega}/r_{s,\Delta\Omega} \ll 1$ is fulfilled. This measurement condition can be easily arranged by applying the clear coat material onto a black substrate.

Alternatively, the method according to the invention may also be performed to determine the refractive index of darkly pigmented, preferably black pigmented, coatings (in the present case comprising the transparent clear coat which has merely been darkly or black pigmented for the purpose of making the measurements) or darkly pigmented, preferably black pigmented binder systems.

The method according to the invention accordingly also relates to a method for the non-destructive determination of the refractive index of un-pigmented or transparent clear coats or un-pigmented binder systems comprising the following steps:

A') pigmenting the un-pigmented or transparently pigmented clear coat or un-pigmented binder system with a dark absorption pigment;

B') application of the darkly pigmented coating or darkly pigmented binder system onto a substrate;

C') optional drying and/or curing of the coating obtained in said manner;

D') acquisition of the reflection spectrum of the coating obtained with a spectrophotometer with d/8° measurement geometry with the specular component included and with the specular component excluded;

E') determination of the differential spectrum between the reflection spectrum with the specular component included and reflection spectrum with the specular component excluded; and, F') determination of the refractive index of the coating or binder system with the assistance of the differential spectrum obtained in E') by making use of a previously determined relationship between the difference between the reflection spectrum with the specular component included and the reflection spectrum with the specular component excluded of the coating or binder system and the refractive index of the corresponding coating or binder system.

The individual steps are performed as already described above. The coating or binder system to be determined is preferably pigmented with a black absorption pigment. The condition for this alternative procedure is, as has likewise already been mentioned above, merely that in the pigmented systems the pigments must not be arranged at the surface of the coating.

The method according to the invention provides a spectrophotometric method for the non-destructive determination of the refractive index of clear coats and binder systems, which method makes it possible to determine relatively straightforwardly in advance on the basis of the refractive index the repairability of original coatings with corresponding repair coatings. Experience has shown that the difference in refractive index between two clear coats ought not to be greater than 0.04, if it is to be ensured, especially on application onto very dark or black colour shades, that the different reflective properties of the surface of the applied clear coats are not perceived visually by an observer.

The following Examples are intended to illustrate the invention in greater detail.

EXAMPLES

Figure 4A:
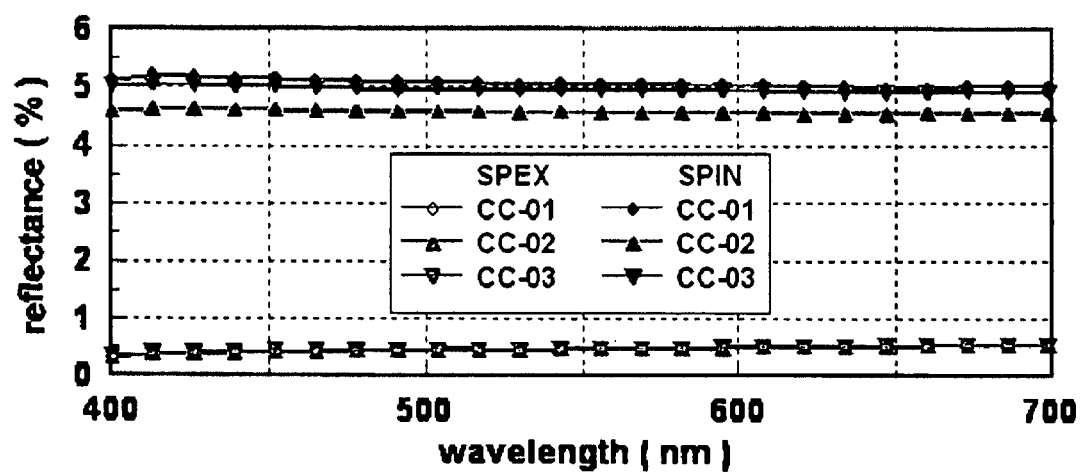
FIG. 4 shows experimentally determined refractive index results of three different clear coats.
Figure 4B:
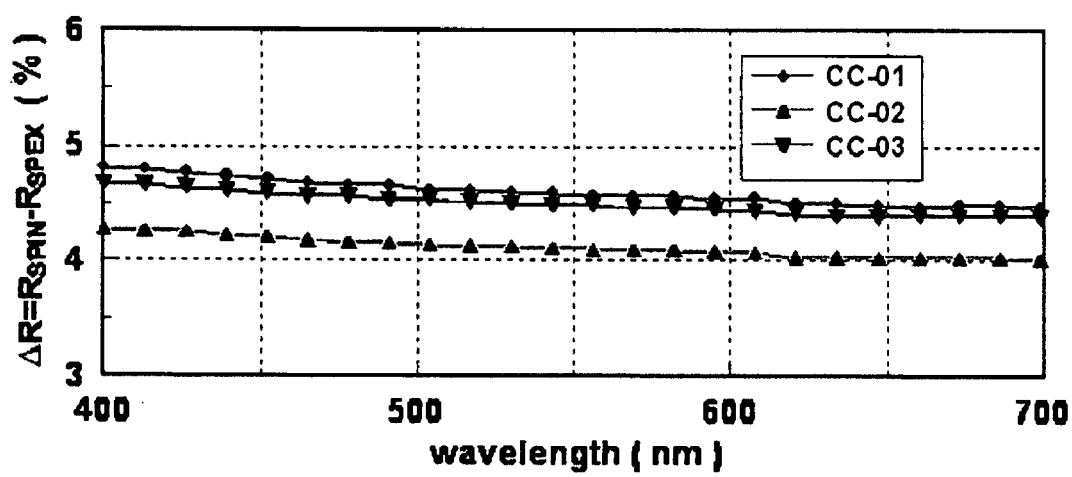
Figure 4C:
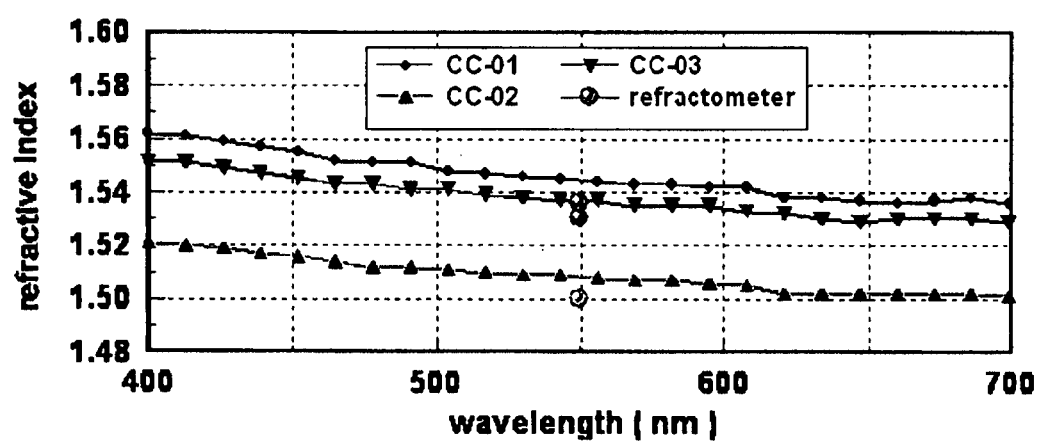

FIG. 4 depicts some experimentally determined refractive index results of three different clear coats (CC-01 to CC-03) obtained from the spectrophotometric method in comparison with corresponding results directly measured by means of a refractometer. The clear coats have been sprayed on a substrate coated with a black base-coat. The upper diagram (Diagram 4/1) displays the wavelength dependence of the reflectance measurements with the specular component included ($R_{SPIN}$) and excluded ($R_{SPEX}$). In the middle diagram (Diagram 4/2) the corresponding difference spectra $\Delta R = R_{SPIN} - R_{SPEX}$ are shown. The lower diagram (Diagram 4/3) shows the derived refractive index n for all three clear coat materials as a function of wavelength. A close scrutiny of FIG. 4 reveals that in all three depicted cases the wavelength dependence of n is weak. The absolute value n varies between 1.50 and 1.56 and decreases by roughly 1% over the sampled wavelength range. In order to determine the difference between the refractive indices of the particular clear coats, it is possible either to use the mean refractive index of the particular clear coat over the entire measured wavelength range or to compare the refractive indices of the particular clear coats at a defined wavelength. In the present Examples, an observer ought not to be able to discern any visual differences between the coatings (with CC-01, CC-02 and CC-03). Particularly advantageously, clear coat CC-01 could be used to repair clear coat CC-02 or conversely clear coat CC-02 to repair clear coat CC-01.

In addition to that the refractive indices obtained from refractometer measurements on self-contained films have been included in FIG. 4 and centered at a wavelength of 550 nm. Actually, these data can not be referred to a particular wavelength, since the refractometer used for the measurements was equipped with an incandescent light source and provides only integrated values over a wavelength range dependent on the sensitivity function of the detector. While the absolute values of both data sets differ by a small offset of approximately 0.04, the spread of the data points in both cases compares favorably. This slight experimental offset can be ascribed to a systematic error of the white calibration tile reflection data table, but this offset is irrelevant for a relative comparison between different clear coat materials. However, this offset information could even be used to refine the photometric scale of the spectrophotometer.

What is claimed is:

1. A method for determining repairabilitly of an original clear coat applied over a darkly pigmented substrate with a corresponding repair clear coat, said method comprises:

A) non-destructively determining the refractive indices of the original clear coat and the corresponding repair clear coat by the steps comprising:

I) acquiring the reflection spectrum of the original clear coat and the corresponding repair clear coat obtained with a spectrophotometer with d/8° measurement geometry with the specular component included and with the specular component excluded;

II) determining the differential spectrum between the reflection spectrum with the specular component included and reflection spectrum with the specular component excluded; and III) determining the refractive index of the original clear coat and the corresponding repair clear coat with the assistance of the differential spectrum obtained in II) by making use of a previously determined relationship between the difference in the reflection spectrum with the specular component included and the reflection spectrum with the specular component excluded of the original clear coat and the corresponding repair clear coat; and B) comparing the refractive index of the original clear coat and the repair clear coat to determine difference between the refractive indices of the original and repair clear coats, wherein when said difference between the refractive indices of the original and repair clear coats is within an acceptable range, the repair clear coat is used to repair the original clear coat.

2. The method of claim 1 wherein said difference between the refractive indices of the original and repair clear coats is not greater than 0.04.

3. The method of claim 1 comprising:

I) applying a transparent layer of an un-pigmented or transparently pigmented coating or an un-pigmented binder system onto said darkly pigmented substrate; and II) drying or curing said transparent layer to obtain said clear repair coat.

4. The method according to claim 1, wherein the darkly pigmented substrate is a black pigmented substrate.

5. The method according to claim 1, wherein the repair clear coat is pigmented with a black absorption pigment.

* * * * *